(12) United States Patent
Geysen et al.

(10) Patent No.: US 6,582,726 B1
(45) Date of Patent: Jun. 24, 2003

(54) CROSS LINKED SOLID SUPPORTS FOR SOLID PHASE SYNTHESIS

(75) Inventors: H. Mario Geysen, Chapel Hill, NC (US); Patrick F. Kiser, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/598,217

(22) Filed: Jun. 21, 2000

(51) Int. Cl.[7] ............................ A61K 9/48; C08G 63/91
(52) U.S. Cl. ............................ 424/451; 525/50
(58) Field of Search ............................ 424/451; 525/50

(56) References Cited

U.S. PATENT DOCUMENTS

| | | | |
|---|---|---|---|
| 5,191,015 A | 3/1993 | Sheppard et al. | |
| 5,916,585 A | 6/1999 | Cook et al. | |

FOREIGN PATENT DOCUMENTS

| | | | |
|---|---|---|---|
| WO | 9726002 | * | 7/1997 |
| WO | WO 97/37953 | | 10/1997 |
| WO | WO 98/01406 | | 1/1998 |

OTHER PUBLICATIONS

Geysen, H.M. et al., "Isotope or mass encoding of combinatorial libraries," *Chemistry & Biology*, Aug. 1996, vol. 3, No. 8, pp. 679–688.

Bennett, William D., Ph.D. et al., "Combinatorial & Solid Phase Organic Chemistory", *Advanced ChemTech Handbook*, 1998, pp. 86–98.

Bunin, Barry A., "Linkers for Solid–Phase Synthesis", *The Combinatorial Index,* Academic Press, 1988, pp. 9–76.

Czarnik, Anthony W. et al., "Specific Implementation of Solid–Phase Synthesis", *A Practical Guide to Combinatorial Chemistry*, American Chemical Society, 1997, pp. 58–97.

Saunders, K.J., "General Methods of Preparation of Polymers", *Organic Polymer Chemistry*, Chapman & Hall, 1988, pp. 5–27.

* cited by examiner

*Primary Examiner*—Alton Pryor
(74) *Attorney, Agent, or Firm*—Michael M. Conger (57) ABSTRACT

A method for performing chemical synthesis includes the steps of providing a solid support having cross links, a first set of cleavable links within the cross links, and a second set of cleavable links having sites on which to perform chemistry. A first chemical is coupled to the chemistry sites, and the first chemical is reacted with a second chemical to produce a reaction product. The links are cleaved to remove the cross links and to cleave the reaction product from the solid support.

24 Claims, 11 Drawing Sheets

CROSS LINKED SOLID SUPPORTS FOR SOLID PHASE SYNTHESIS

BACKGROUND OF THE INVENTION

This invention relates generally to the field of chemistry, and in particular to solid phase chemistry. More specifically, in one aspect the invention relates to solid supports used in solid phase chemistry. In another aspect, the invention relates to polymer based solid supports that may be used to facilitate drug delivery.

Traditionally, experimental chemistries have been performed in solution where various chemicals are reacted while in solution phase. For example, a chemist may desire to perform an experiment to react chemical A with a chemical B to produce a reaction product. To do so using solution phase techniques, the chemist may combine chemical A with chemical B in a solution using a given set of reaction conditions. To increase the rate of the reaction and to insure completion of the chemistry, i.e., maximum conversion of A, an excessive amount of chemical B may be used. However, once the reaction is complete, the excess of chemical B needs to be separated from the product. Such a process can be both difficult and time consuming.

As an alternative to solution phase chemistries, solid phase chemistries have been developed which use solid supports to serve as a "handle" during the synthesis process. Examples of such solid supports are described generally in Anthony W. Czarnick et al., "A Practical Guide to Combinatorial Chemistry," American Chemical Society 1997, the complete disclosure of which is herein incorporated by reference. By using, for example, polystyrene beads, chemical A may be linked to the bead, and an excess of chemical B may be supplied to the bead to drive the chemical reaction at a faster rate and to completion. Following the reaction, the product P may easily be separated from any excess of chemical B since P is physically linked to the bead. Techniques for performing combinatorial chemistry are described generally in Barry A. Bunin, "The Combinatorial Index," Academic Press 1998, the complete disclosure of which is herein incorporated by reference.

However, use of such beads in solid phase chemistries presents other challenges. For example, once chemical B has reacted to form a product, the product needs to be removed from the bead. This may be accomplished, for example, by placing the bead into a reagent that is selected to cleave the product from the bead. Once cleaved, the product then needs to be removed from the bead and the reagent.

Figure 1:
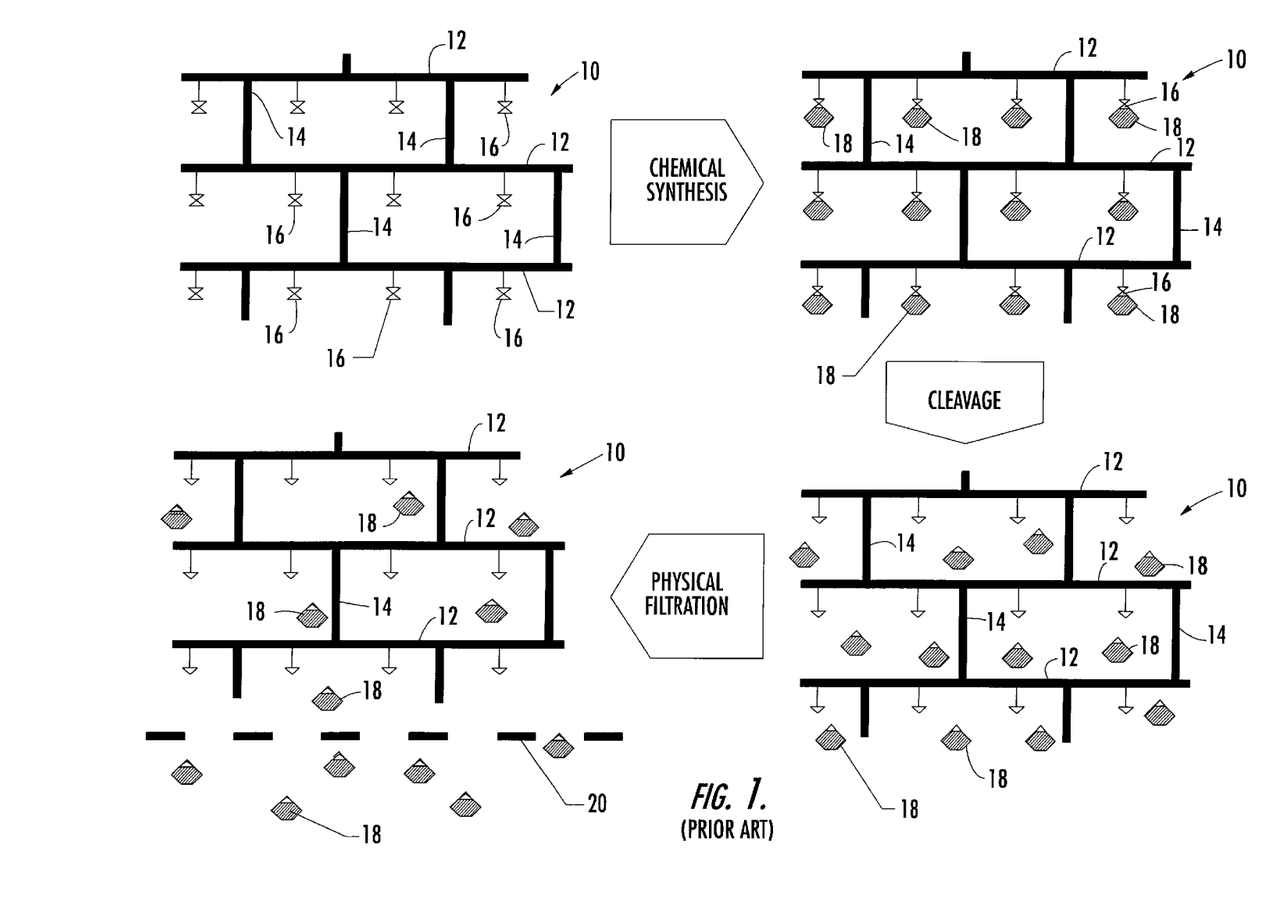
FIG. 1 is a schematic diagram illustrating a prior art chemical synthesis process.

An example of such a process is illustrated in FIG. 1. Shown in FIG. 1 is a solid support 10 that comprises a series of polymer chains 12 that are linked together by cross links 14. The polymer chains 12 also include cleavable links 16 where chemistries are performed. As shown in FIG. 1, chemical synthesis is performed to produce chemical compounds 18 that are coupled to links 16. Compounds 18 are then cleaved from links 18 to remove the compounds 18 from the solid support 10. Following cleavage, the removed compounds 18 are filtered with a filter 20 to separate the compounds from the solid support.

As illustrated in FIG. 1, some of the compounds 18 remain trapped within the solid support. As a result the compounds that remain within solid support 10 are unavailable for use in subsequent procedures. Removal of the compound or product may be challenging for a variety of reasons. For example, transfer of the cleaved product from within the bead to the bulk solution may occur by diffusion. This may introduce a loss of the product if the product has an affinity for the bead and experiences absorption effects during diffusion. As another example, the cleaved product may precipitate within the bead, thereby hindering its removal. At a minimum, an amount of product is left trapped within the interior or the bead in an amount proportional to the solvent volume inside the bead to the volume exterior to the bead.

Hence, the invention relates to the use of solid supports that are configured to facilitate chemical reactions and to efficiently remove chemical products from the solid supports following synthesis. The invention also relates to the use of such solid supports for drug delivery.

SUMMARY OF THE INVENTION

The invention provides solid supports and methods for their construction and use to facilitate the performance of a chemical process or a series of chemical processes or for drug delivery. According to one method, a cross linked solid support is provided having a first set of cleavable links that are present within the cross links and a second set of cleavable links that provide sites on which to carry out chemistry. A first chemical is coupled to the chemistry sites and is then reacted with a second chemical to produce a reaction product. The links are then cleaved to break the cross links and to cleave the reaction product from the solid support. In this way, the un-cross linked solid support is permitted to separate to facilitate removal of the reaction product from the solid support. Conveniently, the first and second cleavable links may be cleaved simultaneously under the same or similar conditions, and may comprise the same or a different chemical entity. Alternatively, the first and second links may be independently cleavable, i.e. orthogonally cleavable, under conditions specific to each link.

Following cleavage, the cleaved reaction product may then be separated from the un-cross linked solid support. For example, the cleaved reaction product may be filtered from the un-cross linked solid support with a filter or a semipermeable membrane.

In some cases, the solid support may be provided with a third set of cleavable links that are present within the cross links and that are orthogonally cleavable relative to the first and/or second set of links. Such a configuration of the solid support permits the third set of cross links to be cleaved while the first and/or second set of links (which are present within the cross links of the solid support and provide the chemistry sites for the attachment of chemicals or chemical products) remain intact. For example, the third set of cross links may be cleaved prior to the first set of links to partially open the solid support to facilitate the entry of materials into the solid support when performing a chemical step or a series of chemical steps. As another example, the third set of cross links may be cleaved to facilitate the performance of an assay, such as a direct binding assay. As a further example, the third set of links may be cleaved to allow access to the products of a reaction by an enzyme to determine if conversion of the reaction product by the enzyme occurs.

In one aspect, the solid support may be constructed of a series of polymer chains that are cross linked by bi-functional reagents containing the cleavable links. In this way, cleavage of the links unlinks the polymer chains.

The invention further provides a solid support for use in performing chemical synthesis. The solid support comprises a series of polymer chains and a set of cleavable links both within the cross links crosslinking the polymer chains and providing chemistry sites. In this way, cleavage of the links both un-cross links the polymer chains and removes any chemicals or chemical products that were previously attached to the chemistry sites. Examples of polymer chains that may be used to construct the solid supports include polymerized styrene, acrylic monomers, ether monomers, and the like.

In one aspect, the solid supports may further include another set of cleavable links within the cross links that are orthogonally cleavable relative to the other set of cleavable links within the cross links. In this way, one set of links may be cleaved while the other set remain intact.

The invention further provides a method for constructing a solid support. According to the method, a set of components are combined in a mixture. The components include a base set of monomers, a set of functional monomers for post polymerization modification, and a set of bivalent cross linking monomers which contain a cleavable link. The components are polymerized to form a plurality of solid supports that each comprise a series of polymer chains and a set of cross links containing cleavable links cross linking the polymer chains. In a further step, a plurality of chemistry site links may be attached to the polymer chains, with the chemistry site links being cleavable under the same conditions as are those within the cross links.

In another embodiment, a solid support for performing chemical synthesis comprises a grafting surface and a set of cleavable links that are attached to the surface. A series of chemical chains on which to attach chemistry links are then attached to the cleavable links.

DESCRIPTION OF THE SPECIFIC EMBODIMENTS

The invention provides various cleavable cross linked solid supports that are constructed to facilitate chemical reactions and to increase the recovery or the separation of any reaction products following synthesis. The solid supports of the invention may be cross linked with a chemical entities which contain a cleavable link and may include other cleavable links that provide sites on which to perform chemistry during synthesis. Cleavable links that may be incorporated within the cross links and as sites for chemistry are described in Anthony W. Czamick et al., "A Practical Guide to Combinatorial Chemistry," American Chemical Society 1997, previously incorporated by reference. Cleavage reactions that may be used to cleave links are described in William D. Bennett et al., "Advanced ChemTech Handbook of Combinatorial and Solid Phase Organic Chemistry," Advanced ChemTech, Inc. 1998, the complete disclosure of which is herein incorporated by reference.

By utilizing such features, the solid supports of the invention may operate in essentially the same manner as the solid supports known to those skilled in the art during the course of carrying out the synthetic steps required to obtain the desired product. In addition, once the reaction product is produced, the cross link may be cleaved to permit the solid support to separate. Such cleavage also clips the reaction product from the solid support. The cleaved product may then be separated from the unlinked solid support using any one of a variety of separation techniques. For example, separation may be accomplished using a filter or a semipermeable membrane to hold back the now non-cross linked remains of the solid support. Another method of separation may be to selectively precipitate the materials used to construct the solid support. Yet another way to maximally separate the product away from the remains of the solid support may be to effect a phase separation using two immiscible solvents such that the now non-cross linked polymer is soluble in one solvent and the product is soluble in the other solvent. Further examples of separation techniques include other size exclusion techniques, ion exchange techniques, affinity techniques, fluorous phase separation, and the like.

Hence, the invention permits the solid supports to have the same properties commonly used with traditional cross linked solid supports, such as those available from Advanced ChemTech, Argonaut, and NovaChem. At the same time, the solid support may be reverted to a series of unlinked chains, such as polymer chains, to facilitate product removal and separation.

The cleavable links within the cross links may conveniently be cleavable under the same conditions as the links used as sites for the chemistry permit both sets of links to be simultaneously cleaved. Conveniently, both sets of links may be formed from the same chemical entity or different chemical entities. Alternatively, the links may be independently cleaved under conditions which permit such cleavage, i.e. the links may be orthogonally cleavable relative to each other. The invention may also utilize additional sets of cleavable links that are incorporated within the cross links. These additional links may be cleavable independently from the other links within the cross links and/or from the links forming the sites for chemistry. Hence, the solid support may include more than one type of cleavable link within the cross links that are orthogonally cleavable, i.e. cleavable under different conditions. In this manner, one set of cross links may be cleaved to "loosen" the solid support while the other links remain uncleaved. In this way, the solid support is permitted to partially expand to facilitate a process which optimally requires a more expanded solid support, or to provide a greater accessibility of the product of a series of chemical reactions to some further process. By keeping some of the cross links intact, the advantages conferred by the use of a solid support are retained.

As another example of the use of orthogonally cleavable links, one set of cross links may be cleaved to permit the solid support to expand. Chemistries may then be performed while the solid support is in the expanded state to facilitate diffusion of the chemicals into the solid support or to allow a greater access to the partial product for the remaining chemical or process steps. The resulting product may then be cleaved at the same time the second set of cross links are cleaved to facilitate product extraction and recovery.

In other cases, one set of links may be used with cross links that cross link the solid support and an orthogonal set of links may be used as the chemistry sites. In this way, a series of reactions may be performed in solid phase. The cross links may then be cleaved and any remaining steps performed in solution phase. The resulting chemical product may then be cleaved and separated.

Another aspect of the solid supports is that they may be used to facilitate drug delivery. For example, the solid supports may be used to form a drug delivery capsule having a drug that is released from the solid support upon cleavage of a link. The capsule may be configured such that its cross links are simultaneously cleaved along with cleavage of the drug. Alternatively, the cross links of the capsule may first be cleaved for a gradual opening of the polymer matrix. Cleavage of the links where the drug is attached then allows for the release of the drug. Further, the links may be selected to control both where cleavage occurs and the rate of release.

The techniques of the invention may be used with a wide variety of solid supports. For example, the solid supports may be constructed of cross linked polymers, styrene, acrylic acid, acylamide, ethers and the like. The type of cross link used is dependent upon the nature of the chemistry and the type of solid support. In one aspect, the cross link may comprise a bi-functional monomer having an incorporated cleavable link.

The invention may be used with other types of solid supports, such as grafted plastic solid surfaces as well. Examples of such solid surfaces are described generally in N. J. Maeji, R. M. Valerio, A. M. Bray, R. A. Campbell, and H. M. Geysen, "Grafted Supports Used with the Multipin Method of Peptide Synthesis", Reactive Polymers, 22, 203–212 (1994); A. M. Bray, R. M. Valerio, A. J. DiPasquale, J. Greig, and N. J. Maeji, "Multiple Synthesis by the Multipin Method as a Methodological Tool", Journal of Peptide Science, Vol. 1 80–87 (1995); A. M. Bray, D. S. Chiefari, R. M. Valerio, and N. J. Maeji, "Rapid Optimization of Organic Reactions on Solid Phase Using the Multipin Approach", Tetraheron Lett 36, 5081–5084 (1995); C. T. Bui, N. J. Maeji, F. A. Rasoul, and A. M. Bray, "A Simple Method for Generation of Chloromethyl Polystyrene on the Multipin Solid Support, Tetrahedron Lett 40 5383–5386 (1999), the complete disclosures of which are herein incorporated by reference. For example, a link may be attached to a plastic surface and polymer chains may then be attached to the link.

Figure 2:
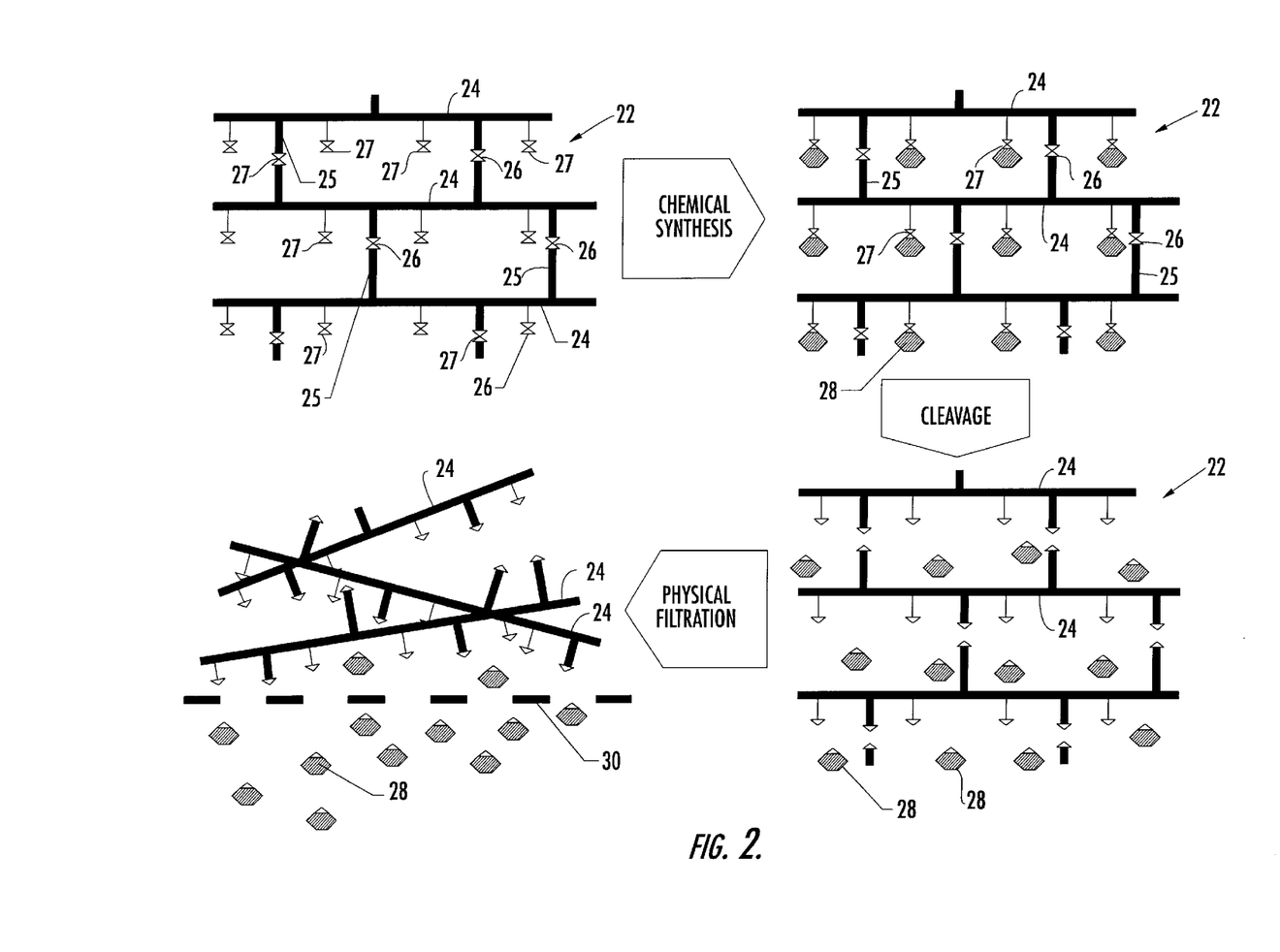
FIG. 2 is a schematic diagram illustrating an exemplary chemical synthesis process according to the invention.

Referring now to FIG. 2, one exemplary method for performing chemical synthesis using a solid support 22 will be described. Solid support 22 is constructed of a plurality of polymer chains 24 that are cross linked by cross links 25 having cleavable links 26. Cross links 25 may comprise bi-functional monomers incorporating links 26. Polymer chains 24 also include cleavable links 27 that serve as sites where chemical compounds 28 may be attached during chemical synthesis as shown. The ratio of the number of cleavable links 26 to the number of cleavable links 27 may be in the range from about $1:10^{12}$ to about 1:1. Further, links 26 and 27 may or may not be constructed from the same chemical entity.

Following synthesis, chemical compounds 28 are cleaved from polymer chains 24 by clipping links 27, e.g. by using an appropriate reagent and appropriate conditions. Cleavage of compounds 28 may also simultaneously cleave links 26 that cross link polymer chains 24. In this way, polymer chains 24 are free to separate to facilitate removal of compounds 28 from the now unlinked solid support. Compounds 28 may then be filtered using a filter 30. Although links 26 and 27 may be cleaved simultaneously, it will be appreciated that links 26 and 27 may be independently cleavable under appropriate conditions.

Use of solid support 22 is advantageous in that it provides a convenient handle for performing chemical synthesis as is known in the art. In this way, solid support 22 maintains all of the features useful with solid phase chemistry as is known in the art. However, support 22 provides the additional advantage of facilitating removal of the compound following synthesis. In this way, loss of the compound is limited even if the compound has an affinity for the bead since absorption effects often experienced during diffusion are now limited. Further, if the cleaved compound precipitates, polymer chains 24 are free to separate to facilitate removal of the precipitated compound.

In some cases, solid support 22 may be used in traditional solution phase chemistries as well. For example, one or more synthesis steps may be performed while links 26 are intact. In the event that a further step is difficult to perform using solid phase chemistry techniques, links 27 may be cleaved to separate the compound from the polymer chains. One or more additional chemistry steps may then be performed on the released compound in solution as is known in the art.

Figure 2A:
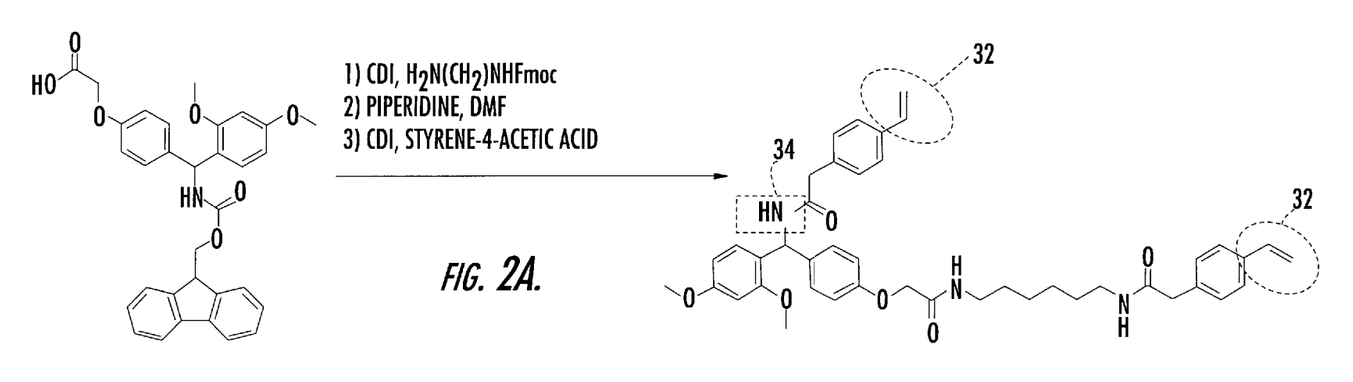
FIG. 2A illustrates one example of how to prepare a styrene based solid support having cross links incorporating cleavable links.
Figure 2B:
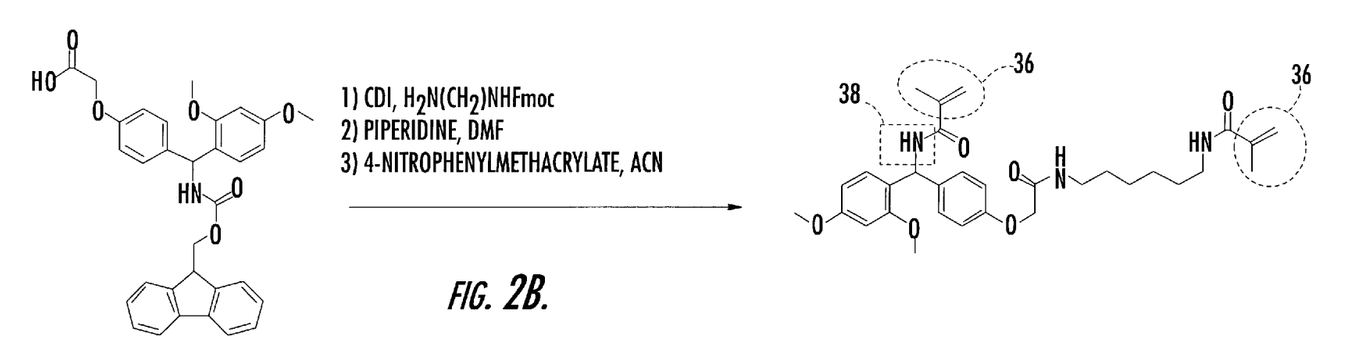
FIG. 2B illustrates another example of how to prepare a styrene based solid support having cross links incorporating cleavable links.

FIGS. 2A and 2B illustrate two non-limiting methods for preparing styrene-based solid supports having cross links with cleavable links. In FIG. 2A, box 32 represents chemical groups that are involved in cross linking the resin. Box 34 represents a cleavable link within the cross link. In FIG. 2B, box 36 represents chemical groups that are involved in cross linking the resin, and box 38 represents a cleavable link within the cross link.

Figure 3:
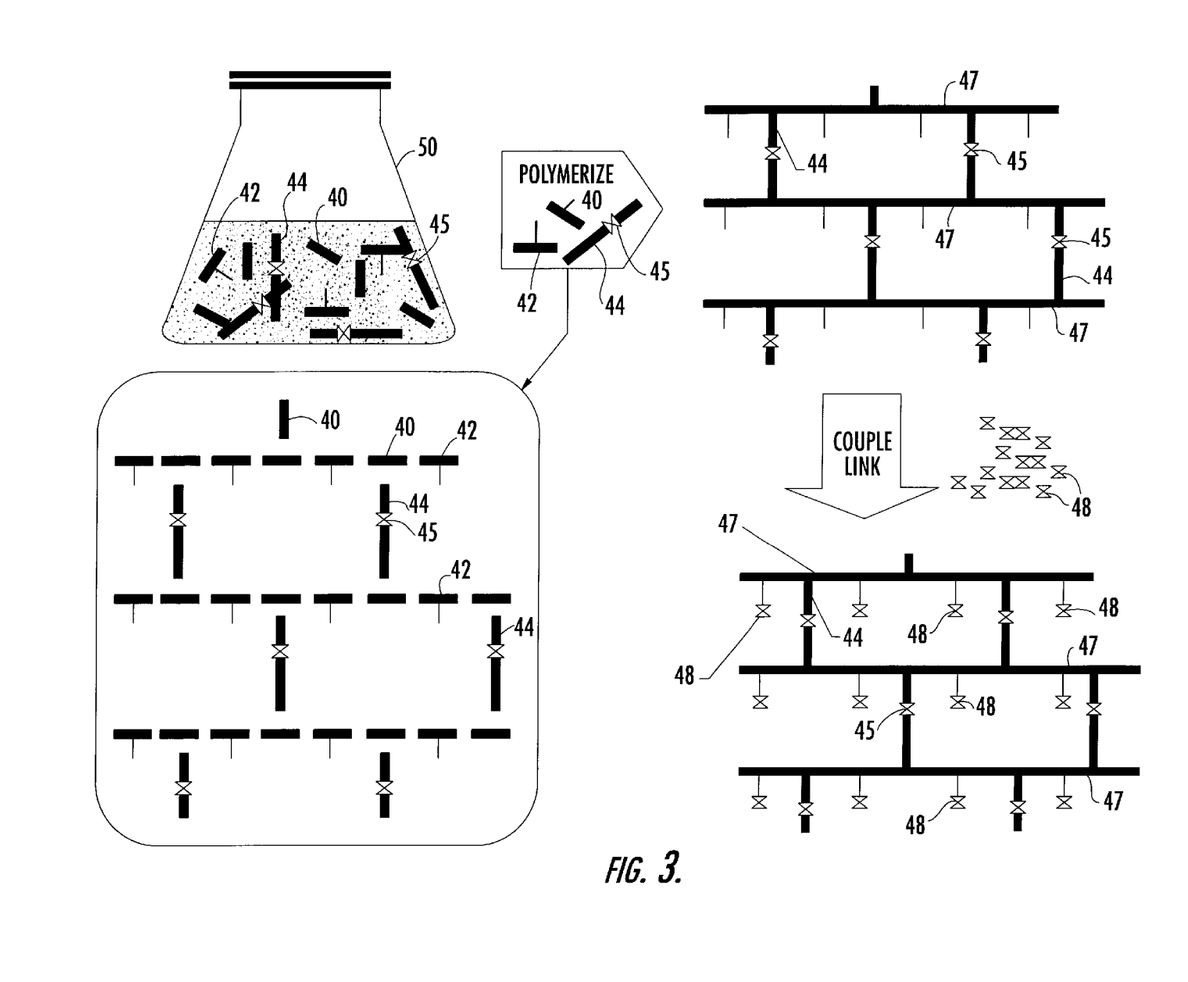
FIG. 3 is a schematic diagram illustrating one method for producing a solid support used in the process of FIG. 2 according to the invention.

Referring now to FIG. 3, one method for making a solid support that is similar to solid support 22 of FIG. 2 will be described. The process begins by combining sets of components 40, 42 and 44 in a container 50, such as a flask. Set 40 comprises a base set of monomers, set 42 comprises a set of functional monomers for post polymerization modification, and set 44 comprises a set of bivalent cross linking monomers which contain a cleavable link 45. The components are then polymerized using techniques known within the art. After polymerization, a set of random copolymer backbones 47 are formed that are cross linked by links 44 having cleavable links 45. Chemistry is then performed to couple links 48 to backbones 47 which serve as sites where chemical synthesis occurs as previously described. The resulting solid supports typically precipitate and are thus easily removed from the remaining liquid in container 26.

Figure 4:
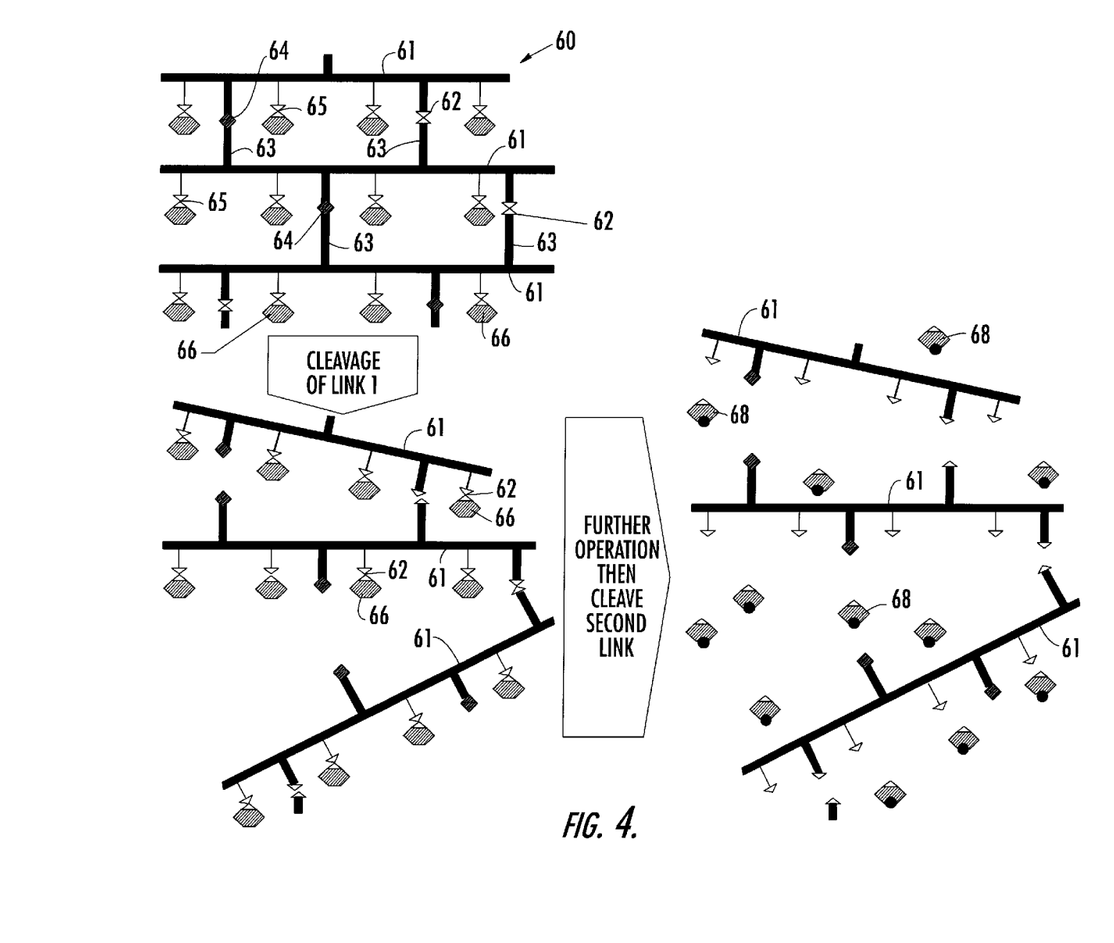
FIG. 4 is a schematic diagram illustrating another chemical synthesis process according to the invention.

FIG. 4 illustrates another embodiment of a solid support 60 that includes two sets of orthogonally cleavable links within the cross links, i.e. links that are cleavable under different sets of conditions, such as by using different reagents or conditions. Solid support 60 is constructed of a set of polymer chains 61 that are cross linked by cross links 63 which incorporate cleavable links 62 or 64. Additional links 65 serve as chemistry sites and, in this embodiment, are cleavable under the same conditions as links 62 which are within the cross links that cross link polymer chains 61 in a manner similar to that previously described in connection with solid support 22. However, solid support 60 differs from solid support 22 in that solid support 60 includes another set of cleavable links 64 within cross links 63 that are orthogonally cleavable relative to links 62.

In one use of solid support 60, chemical compounds 66 are attached to links 65 that form the chemistry sites as shown. Links 64 may then be cleaved to partially open solid support 60 to facilitate the entry of materials into the structure. Complete separation of polymer chains 61 is prevented by links 62. Further, compounds 66 also remain attached to links 65. One or more operations may then be performed while solid support 60 is in such a state. For example, additional chemistries may be performed to produce compounds 68. By having a partially opened solid support, the concentration of the reactant may be reduced. Further, by partially opening the solid support, the size of the synthesized chemical may be increase due to the increase in available spaced within the solid support. Other operations that may be performed include direct binding assays, enzymatic conversion, and the like.

Following completion of the different operations, links 62 are cleaved to completely separate polymer chains 61 and to release compounds 68. The released compounds may then be separated in a manner similar to that previously described in connection with FIG. 2.

Figure 5:
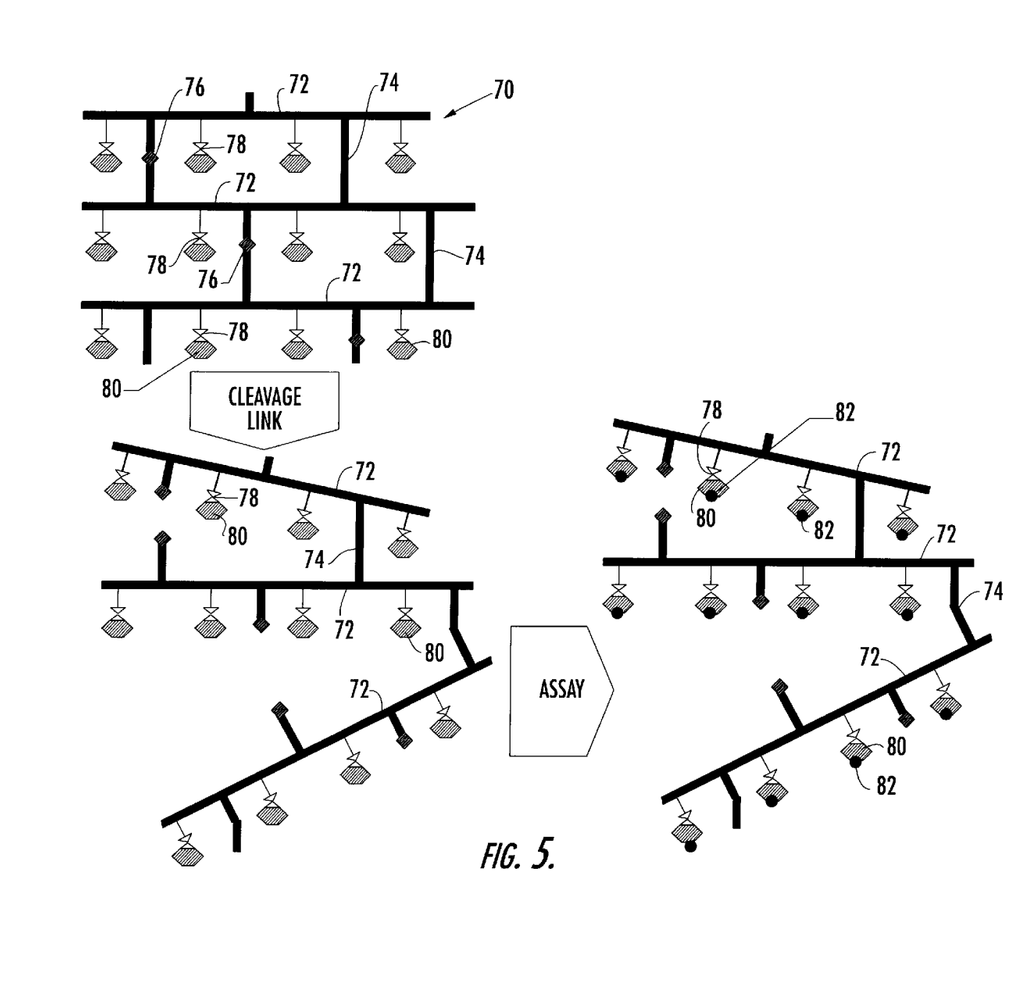
FIG. 5 is a schematic diagram illustrating a process for performing an assay according to the invention.

FIG. 5 illustrates yet another embodiment of a solid support 70 that is constructed of a plurality of polymer chains 72 that are cross linked by cross links 74, some of which include cleavable links 76. Of course, it will be appreciated all or some of cross links 74 may incorporate cleavable links 76. Solid support 70 also includes a set of links 78 that serve as chemistry site links where chemical compounds 80 are attached. Conveniently, links 78 may be orthogonally cleavable relative to links 76. Such a configuration is particularly useful in permitting solid support 70 to be partially opened when links 76 are cleaved to facilitate the entry of materials into solid support 70. Polymer chains 72 remain linked by links 74 to prevent their complete separation, and links 78 remain linked to compounds 80.

As one specific example, assays may be performed to determine chemical activity when solid support 70 is partially opened. For example, direct binding assays may be performed where a receptor or a binding entity 82 is introduced to solid support 70. Because solid support 70 is partially opened, the binding entity 82 may more easily diffuse into solid support 70 to bind with compounds 80. In this way, a stronger signal may be produced, resulting in easier detection.

Figure 6:
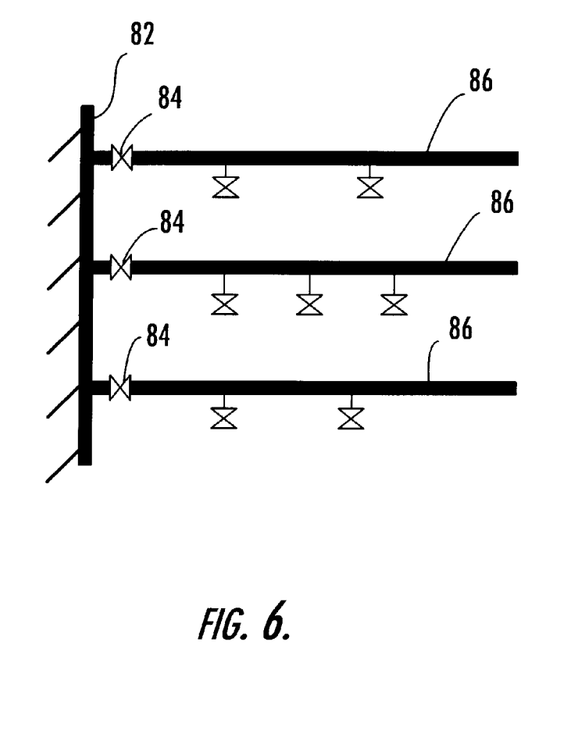
FIG. 6 is a schematic diagram of a grafted plastic solid surface according to the invention.

FIG. 6 illustrates a grafting surface 82 to which are coupled a set of cleavable links 84. Grafting surface 82 may be constructed of materials such as polypropylene, as well as those described in N. J. Maeji, R. M. Valerio, A. M. Bray, R. A. Campbell, and H. M. Geysen, "Grafted Supports Used with the Multipin Method of Peptide Synthesis", Reactive Polymers, 22, 203–212 (1994); A. M. Bray, R. M. Valerio, A. J. DiPasquale, J. Greig, and N. J. Maeji, "Multiple Synthesis by the Multipin Method as a Methodological Tool", Journal of Peptide Science, Vol. 1 80–87 (1995); A. M. Bray, D. S. Chiefari, R. M. Valerio, and N. J. Maeji, "Rapid Optimization of Organic Reactions on Solid Phase Using the Multipin Approach", Tetraheron Lett 36, 5081–5084 (1995); C. T. Bui, N. J. Maeji, F. A. Rasoul, and A. M. Bray, "A Simple Method for Generation of Chloromethyl Polystyrene on the Multipin Solid Support, Tetrahedron Lett 40 5383–5386 (1999), and the like. After coupling links 84 to surface 82, polymerization may occur to couple polymer chains 86 to links 84. To place into solution, links 84 are cleaved to separate polymer chains 86 from surface 82.

Figure 7:
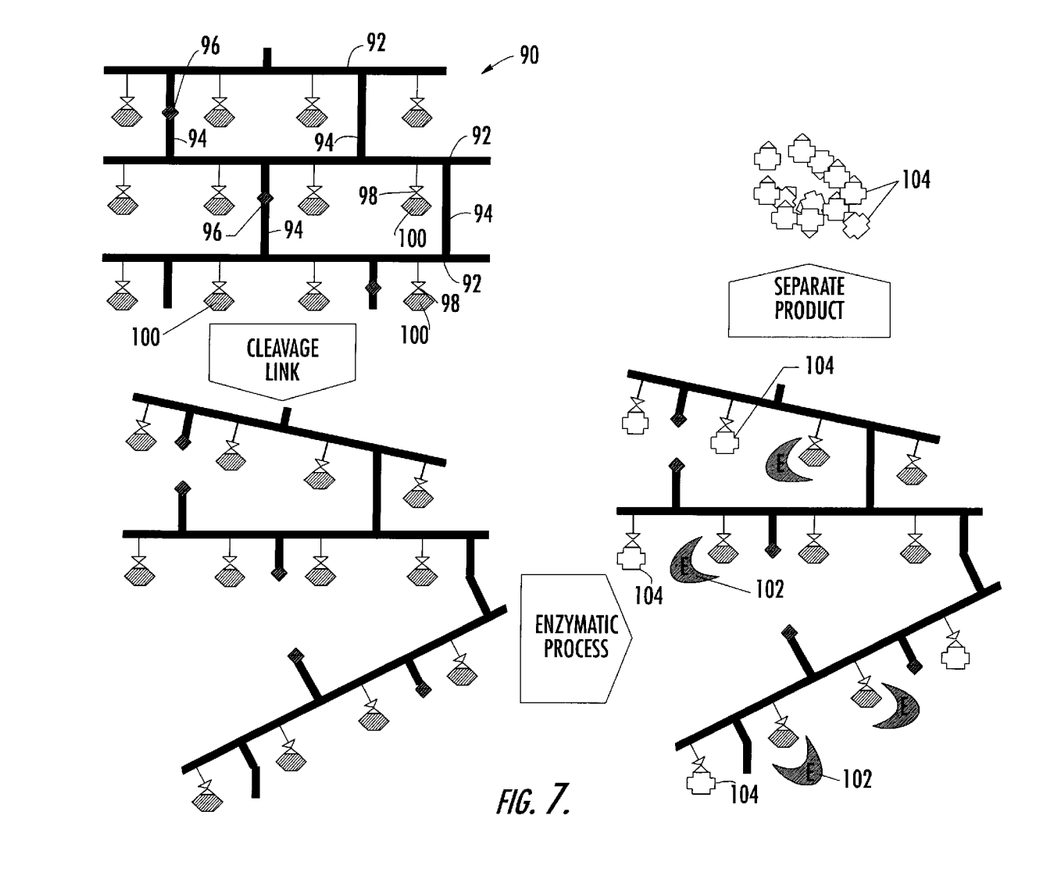
FIG. 7 is a schematic diagram of a chemical synthesis process utilizing an enzymatic process according to the invention.

FIG. 7 illustrates a chemical synthesis process which utilizes an enzyme. The processes utilizes a solid support 90 that comprises polymer chains 92 that are cross linked by cross links 94. Some of cross links 94 include cleavable links 96. Links 98 which serve as links on which chemical compounds 100 have previously been coupled are also provided. Links 96 are cleaved to partially open the polymer matrix as shown in FIG. 7. An enzyme 102 is then added to covert compounds 100 to a reaction product 104. Product 104 may then be cleaved from polymer chains 92.

Figure 8:
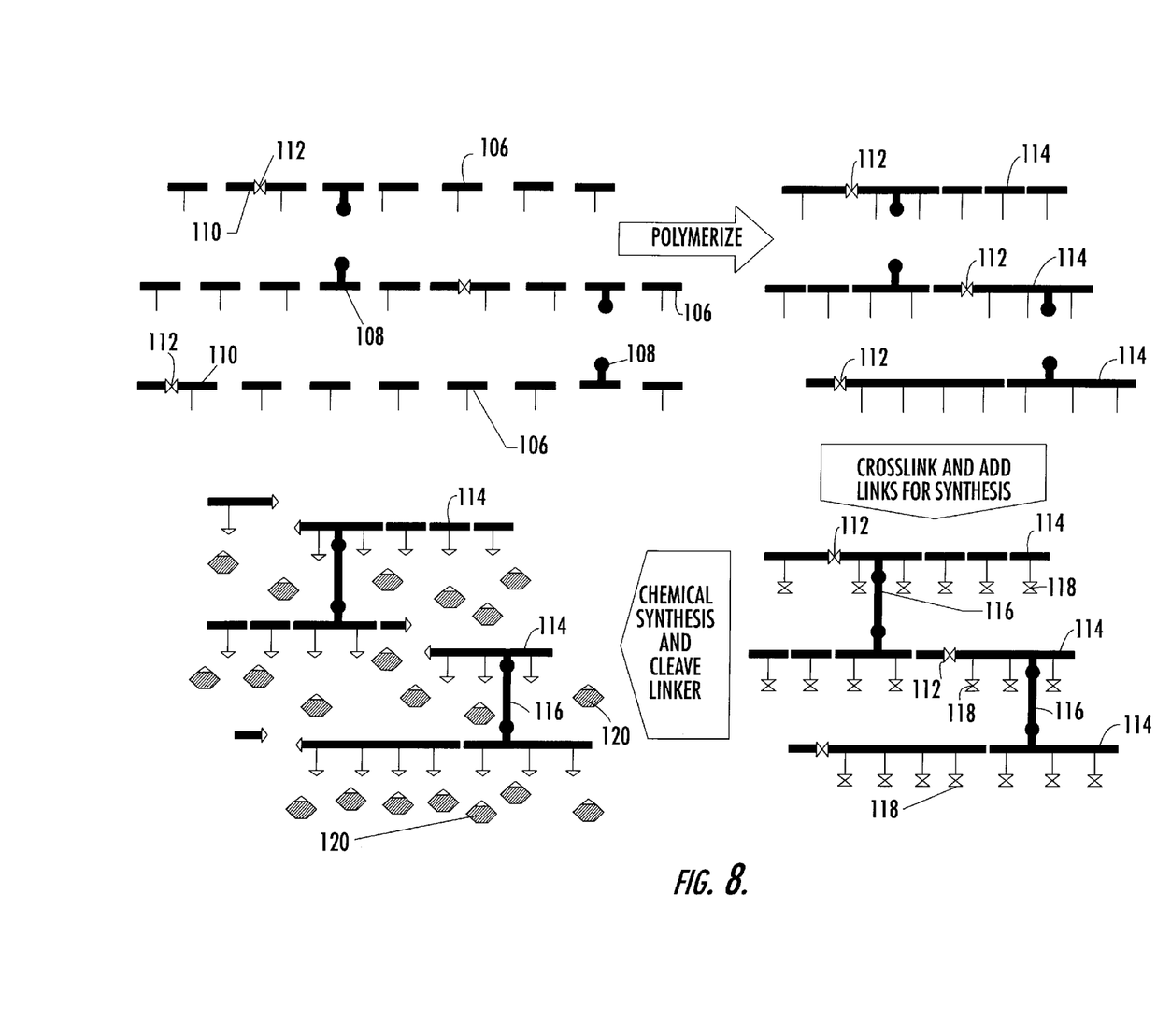
FIG. 8 is a schematic diagram of an alternative chemical synthesis process according to the invention.

FIG. 8 illustrates an alternative method for producing a cleavable synthesis polymer. The process begins by combining a set of unlinked monomers 106, a set of cross link monomers 108, and a set of monomers 110 which contain a cleavable link 112. The components are polymerized to form a set of polymer chains 114 that include cleavable link 112. Polymer chains 114 are then cross linked with cross links 116 and cleavable links 118 are added to create sites where chemistry will be performed. Chemical synthesis is then performed to synthesize compounds 120 onto links 118. Following synthesis, links 112 and 118 are cleaved to break the polymer chains 114 and to release compounds 120. Conveniently, links 112 and 118 may be configured to simultaneous cleave under the same conditions. Alternatively, links 112 and 118 may be configured to be orthogonally cleavable relative to each other.

Figure 9:
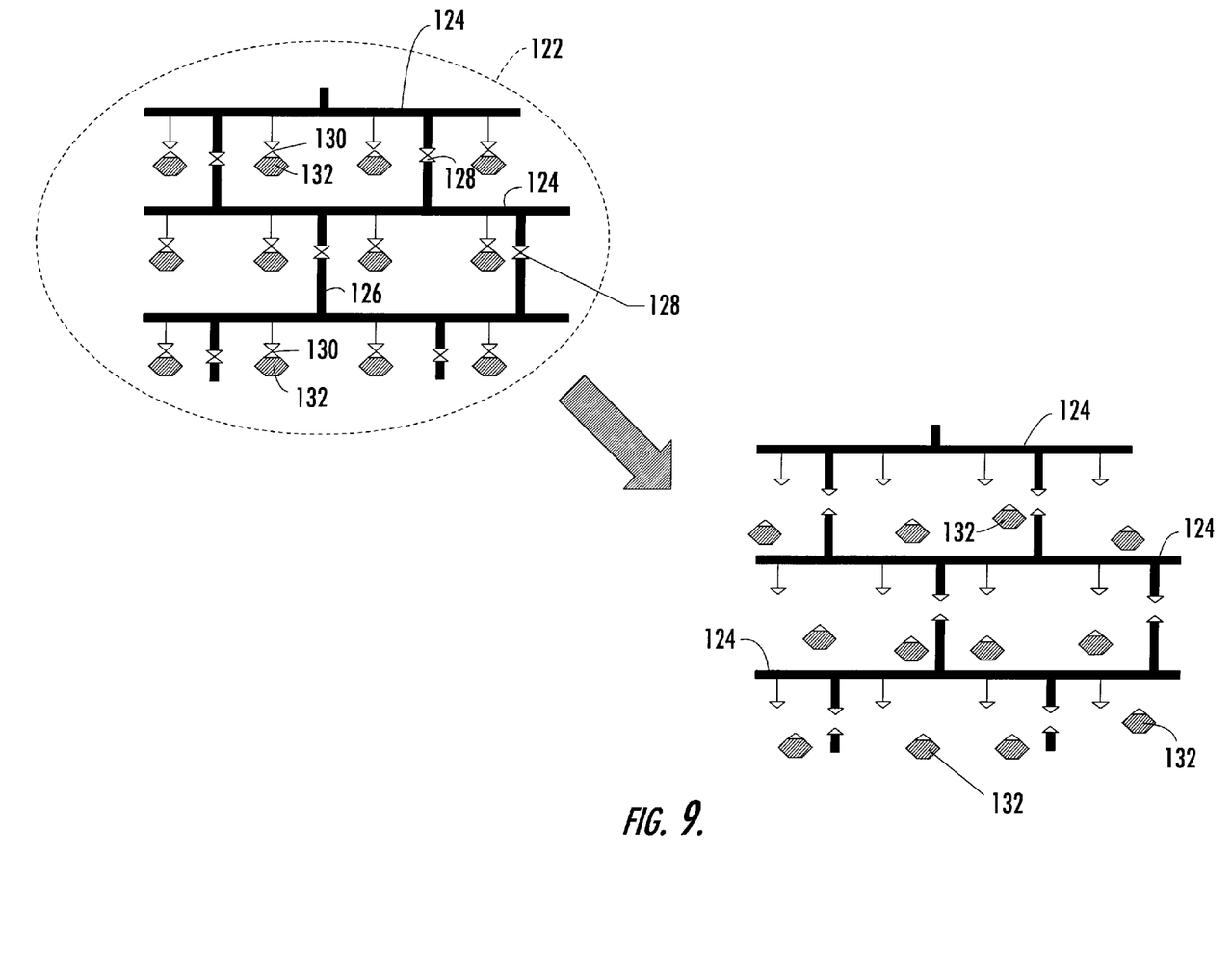
FIG. 9 is a schematic diagram of a formulated drug delivery capsule according to the invention.

The solid supports of the invention may also be utilized for drug delivery. For example, illustrated in FIG. 9 is a drug delivery capsule 122 that is constructed from polymer chains 124 that are cross linked by cross links 126 having cleavable links 128 in a manner similar to that previously described with other embodiments. Cleavable links 130 are also provided and serve at sites where a drug 132 is attached. Links 128 and 130 are configured to permit the polymer matrix to gradually open up and to permit the drug to be released upon cleavage of the links.

Figure 10:
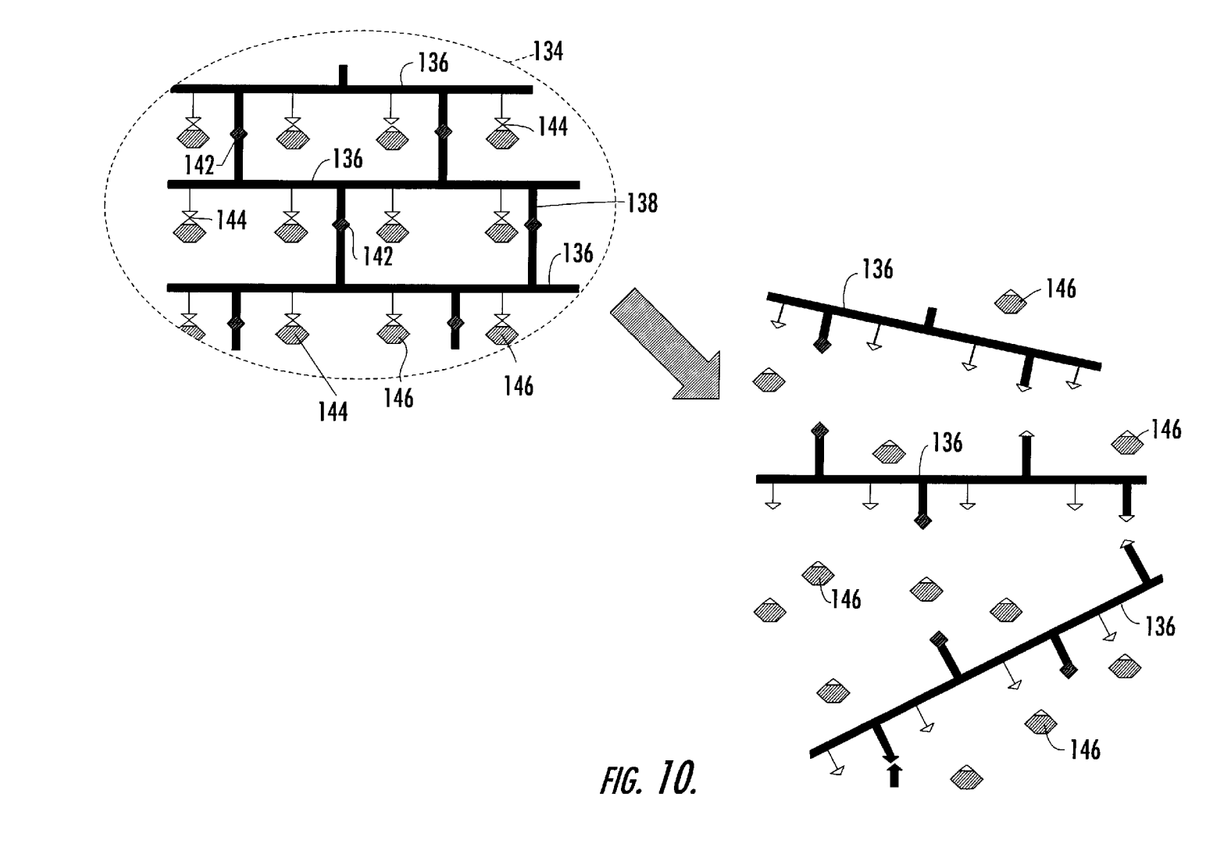
FIG. 10 is a schematic diagram of another formulated drug delivery capsule according to the invention.

FIG. 10 illustrates a drug delivery capsule 134 that is constructed from polymer chains 136 that are cross linked by cross links 138 having cleavable links 142. Cleavable links 144 are also provided and serve at sites where a drug 146 is attached. Links 144 are configured to be orthogonally cleavable relative to links 142. In this way, cleavage of links 142 permits the polymer matrix to gradually open, and cleavage of links 144 permits drug 146 to be released. Hence, the choice of links may be used to control both where cleavage occurs and the rate at which the drug is released from the polymer matrix.

The use of cleavable cross linkers to cross link polymer chains may also be used to construct biodegradable materials. For example, the cross links may be cleavable under certain conditions normally experienced in nature. For instance, the cross links may be cleavable if subjected to a water for a certain length of time. In this way, the materials may break down over time when placed in a land fill.

The invention has now been described in detail for purposes of clarity and understanding. However, it will be appreciated that certain changes and modifications may be practiced within the scope of the appended claims.

What is claimed is:

1. A method for performing chemical synthesis, the method comprising:

providing a solid support having a plurality of cross links, a first set of cleavable links within the cross links, and a second set of cleavable links that provide sites on which to carry out chemistry;

coupling a first chemical to the chemistry sites;

reacting the first chemical with a second chemical to produce a reaction product; and cleaving the first links to remove the cross links and to permit the solid itself to separate and cleaving the second links to cleave the reaction product from the solid support.

2. A method as in claim 1, further comprising cleaving the first and second links under the same conditions.

3. A method as in claim 1, further comprising separating the cleaved reaction product from the un-cross linked solid support.

4. A method as in claim 3, wherein the separating step comprises filtering the cleaved reaction product from the un-cross linked solid support with a filter or a semi-permeable membrane.

5. A method as in claim 3, wherein the separating step comprises selectively precipitating the un-cross linked solid support and separating out the product by filtration or by centrifugation followed by decantation.

6. A method as in claim 1, further comprising providing the solid support with a third set of cleavable links that are orthogonally cleavable relative to the first set of links such that the solid support remains cross linked by the first set of links during cleavage of the third set of links.

7. A method as in claim 6, further comprising cleaving the third set of links prior to cleaving the first set of links and prior to carrying out a further chemical step or a series of chemical steps.

8. A method as in claim 7, wherein the further step comprises introducing an enzyme to the product to determine if conversion of the reaction product by the enzyme occurs.

9. A method as in claim 1, wherein the solid support comprises a series of cross linked polymer chains, and wherein the cleaving step unlinks the polymer chains.

10. A method for performing chemical synthesis, the method comprising:

providing a series of polymer chains that are cross linked by cross links having a first set of cleavable links;

attaching a second set of cleavable links to the polymer chains that provide sites on which to carry out chemistry;

performing chemistry on the sites to produce one or more reaction products; and cleaving the first set of links to unlink the polymer chains and to permit the polymer chains themselves to separate and cleaving the second set of links to cleave the reaction products from the chemistry sites.

11. A method for performing chemical synthesis, the method comprising:

providing a plurality of solid supports that each comprise a series of polymer chains that are cross linked with cross links having a first set of cleavable links and a second set of cleavable links that provide sites on which to carry out chemistry;

performing chemistry on the sites to produce one or more reaction products; and cleaving the first and second set of links to unlink the polymer chains and to cleave the reaction products from the chemistry sites.

12. A solid support for performing chemical synthesis, comprising:

a series of polymer chains cross linked by cross links; and a first set of cleavable links within the cross links; and a second set of cleavable links that provide sites on which to carry out chemistry.

13. A solid support as in claim 12, wherein the first and second sets of cleavable links are cleavable under similar conditions.

14. A solid support as in claim 12, further comprising a first chemical attached to the chemistry sites.

15. A solid support as in claim 12, further comprising a reaction product attached to the chemistry sites.

16. A solid support as in claim 12, wherein the polymer chains are selected from a group consisting of polymerized vinylic, amido, esters, amines, acrylic, and ether containing monomers.

17. A solid support as in claim 12, wherein the ratio of the first set of cleavable links to the second set of cleavable links is in the range from about $1:10^{12}$ to about 1:1.

18. A solid support as in claim 12, further comprising a third set of cleavable links within the cross links that are orthogonally cleavable relative to the first set of cleavable links.

19. A method for constructing a solid support, the method comprising:

combining a set of components in a mixture, the components including a base set of monomers, a set of functional monomers for post polymerization modification, and a set of bivalent cross linking monomers which contain a cleavable link; and polymerizing the components to form a plurality of solid supports that each provide a series of random or block co-polymer backbones that are cross linked by cross links having a set of cleavable links within the crosslinks; and attaching a plurality of cleavable chemistry site links to the polymer chains.

20. A method as in claim 19, further comprising attaching a plurality of chemistry site links to the polymer chains, wherein the chemistry site links are cleavable under the same conditions as are the cleavable links within the cross links.

21. A method for constructing a solid support, the method comprising:

placing a set of components in a mixture, wherein the components comprise a base set of monomers which include monomer containing cleavable links, and monomers used for post-polymerization chemical modification and crosslinking;

polymerizing the components to form linear polymers that each comprise a series of copolymer backbones with cleavable links within crosslinks;

initiating crosslinking to form a plurality of solid supports that contain the cleavable links in the backbone and non-cleavable links between the backbones; and attaching a plurality of cleavable chemistry site links to the polymers.

22. A drug delivery capsule, comprising a capsule having:
a series of polymer chains cross linked by cross links;
a first set of cleavable links within the cross links;
a second set of cleavable links; and
a drug attached to the second set of cleavable links.

23. A solid support as in claim 22, wherein the first and second sets of cleavable links are cleavable under similar conditions.

24. A capsule as in claim 22, wherein the first and second set of cleavable links are cleavable under different conditions.

* * * * *